(12) United States Patent
Hallakou-Bozec (10) Patent No.: US 11,617,754 B2
(45) Date of Patent: Apr. 4, 2023

(54) METHODS OF TREATING HEART FAILURE WITH PRESERVED EJECTION FRACTION

(71) Applicant: Poxel SA, Lyons (FR)

(72) Inventor: Sophie Hallakou-Bozec, Antony (FR)

(73) Assignee: Poxel SA, Lyons (FR)

( * ) Notice: Subject to any disclaimer, the term of this patent is extended or adjusted under 35 U.S.C. 154(b) by 9 days.

(21) Appl. No.: 16/652,911

(22) PCT Filed: Oct. 2, 2018

(86) PCT No.: PCT/IB2018/057648
§ 371 (c)(1),
(2) Date: Apr. 1, 2020

(87) PCT Pub. No.: WO2019/069230
PCT Pub. Date: Apr. 11, 2019

(65) Prior Publication Data
US 2020/0316078 A1    Oct. 8, 2020

Related U.S. Application Data

(60) Provisional application No. 62/566,668, filed on Oct. 2, 2017.

(51) Int. Cl.
| | | |
|---|---|---|
| *A61K 31/53* | (2006.01) | |
| *A61P 9/04* | (2006.01) | |
| *A61K 9/00* | (2006.01) | |
| *A61K 45/06* | (2006.01) | |

(52) U.S. Cl.
CPC ............ *A61K 31/53* (2013.01); *A61K 9/0053* (2013.01); *A61K 45/06* (2013.01); *A61P 9/04* (2018.01)

(58) Field of Classification Search
CPC ..................................................... A61K 31/53
See application file for complete search history.

(56) References Cited

U.S. PATENT DOCUMENTS

| | | |
|---|---|---|
| 7,034,021 B2 | 4/2006 | Moinet et al. |
| 7,452,883 B2 | 11/2008 | Moinet et al. |
| 7,501,511 B2 | 3/2009 | Moinet et al. |
| 7,767,676 B2 | 8/2010 | Moinet et al. |
| 8,217,040 B2 | 7/2012 | Moinet et al. |
| 8,227,465 B2 | 7/2012 | Moinet et al. |
| 8,461,331 B2 | 6/2013 | Helmreich et al. |
| 8,592,370 B2 | 11/2013 | Mesangeau et al. |
| 8,742,102 B2 | 6/2014 | Helmreich et al. |
| 8,742,103 B2 | 6/2014 | Cravo et al. |
| 8,791,115 B2 | 7/2014 | Moinet et al. |
| 8,846,911 B2 | 9/2014 | Maillard et al. |
| 8,937,066 B2* | 1/2015 | Mesangeau ............... A61P 9/06 514/245 |
| 8,980,828 B2* | 3/2015 | Mesangeau ............... A61P 3/06 514/6.5 |
| 9,035,048 B2 | 5/2015 | Cravo et al. |
| 9,211,263 B2* | 12/2015 | Baron .................... A61K 9/2846 |
| 9,271,984 B2* | 3/2016 | Fouqueray ............ A61K 9/2027 |
| 2013/0131065 A1* | 5/2013 | Fouqueray ............ A61K 9/2054 514/245 |
| 2013/0177604 A1 | 7/2013 | Baron et al. |
| 2015/0246045 A1 | 9/2015 | Klein et al. |
| 2017/0119853 A1 | 5/2017 | Shannon |
| 2017/0266152 A1 | 9/2017 | Broedl et al. |
| 2017/0304262 A1 | 10/2017 | Nalk et al. |

FOREIGN PATENT DOCUMENTS

| | | |
|---|---|---|
| WO | WO-2009095159 A1 | 8/2009 |
| WO | WO-2009141040 A2 | 11/2009 |
| WO | WO-2010012746 A2 | 2/2010 |
| WO | WO-2010066901 A2 | 6/2010 |
| WO | WO-2011006984 A1 | 1/2011 |
| WO | WO-2011154497 A1 | 12/2011 |
| WO | WO-2012072663 A1 | 6/2012 |
| WO | WO-2014161919 A1 | 10/2014 |
| WO | WO-2019069230 A1 | 4/2019 |
| WO | WO-2019236844 A1 | 12/2019 |

OTHER PUBLICATIONS

Banquet, S., et al., "Arteriogenic therapy by intramyocardial sustained delivery of a novel growth factor combination prevents chronic heart failure," *Circulation* 124(9):1059-1069, Lippincott Williams and Wilkins Ltd., United States (2011).

Ceia, F., et al., "Prevalence of chronic heart failure in Southwestern Europe: the EPICA study," *Eur J Heart Failure* 4(4):531-539, Wiley-Blackwell, United States (2002).

Devereux, R.B., et al., "Congestive heart failure despite normal left ventricular systolic function in a population-based sample: the Strong Heart Study," *Am J Cardiol* 86(10):1090-1096, Elsevier Inc., United States (2000).

Dubourg, J., et al., "Imeglimin monotherapy in Japanese patients with type 2 diabetes: results from a randomized, 24-week, double-blind, placebo-controlled, phase IIb trial," *53$^{rd}$ EASD Annual Meeting of the European Association for the Study of Diabetes* (Sep. 11-15, 2017), Session PS066 Novel Approaches to glucose-lowering: Poster 843, 1 page (2017).

Dubourg, J., et al., "843—Imeglimin monotherapy in Japanese patients with type 2 diabetes: results from a randomised, 24-week, double-blind, placebo controlled, phase IIb trial," *53$^{rd}$ EASD Annual Meeting of the European Association for the Study of Diabetes* (Sep. 11-15, 2017), Session F—PS066 Novel Approaches to Glucose-Lowering: Abstract 843, 1 page (2017).

(Continued)

*Primary Examiner* — Rei Tsang Shiao (74) *Attorney, Agent, or Firm* — Goodwin Procter LLP (57) ABSTRACT

The present invention provides a method for treating or preventing heart failure with preserved ejection fraction (HFPEF), wherein the method comprises administering to a patient having or at risk of developing HFPEF a therapeutically effective amount of imeglimin.

22 Claims, 6 Drawing Sheets

(56) References Cited

OTHER PUBLICATIONS

Fang, Y., et al., "Improvement of left ventricular diastolic function induced by β-blockade: a comparison between nebivolol and metoprolol," *Journal of Molecular and Cellular Cardiology* 51(2):168-176, Academic Press Inc., United States (2011).

Fang, Y.H., et al., "Heart rate reduction induced by the if current inhibitor ivabradine improves diastolic function and attenuates cardiac tissue hypoxia," *Journal of Cardiovascular Pharmacology* 59(3):260-267, Lippincott Wiliams and Wilkins Ltd., United States (2012).

Fonarow, G.C., et al., "Characteristics, treatments, and outcomes of patients with preserved systolic function hospitalized for heart failure: a report from the OPTIMIZE-HF Registry," *J Am College Cardiol* 50(8):768-777, Elsevier, Netherlands (2007).

Fraccarollo, D., et al., "Improvement in left ventricular remodeling by the endothelial nitric oxide synthase enhancer A VE9488 after experimental myocardial infarction," *Circulation* 118:818-827, Lippincott Williams and Wilkins Ltd., United States (2008).

From, A.M., et al., "Heart Failure with Preserved Ejection Fraction: Pathophysiology and Emerging Therapies," *Cardiovascular Therapeutics* 29(4):E6-E21, Wiley-Blackwell Publishing Ltd., United Kingdom (2011).

Gillebert, T.C., et al., "Intracavitary ultrasound impairs left ventricular performance: presumed role of endocardial endothelium," *Am J Physiol* 263(6):H857-H865, American Physiological Society, United States (1992).

Gomez, E., et al., "Reduction of heart failure by pharmacological inhibition or gene deletion of protein tyrosine phosphatase 1B," *Journal of Molecular and Cellular Cardiology* 52(6):1257-1264, Academic Press Inc., United States (2012).

International Search Report and Written Opinion for International Application No. PCT/IB2018/057648, European Patent Office, Netherlands, dated Jan. 22, 2019, 11 pages.

Kitzman, D.W., et al., "Importance of heart failure with preserved systolic function in patients > or=65 years of age. CHS Research Group. Cardiovascular Health Study," *Am J Cardiol* 87(4):413-419, Elsevier Inc., United States (2001).

Komajda, M., and Lam, C.S.P., "Heart failure with preserved ejection fraction: a clinical dilemma," *Eur Heart J* 35(16):1022-1032, Oxford University Press, United Kingdom (2014).

Lachaux, M., "P577 Short- and long-term imeglimin treatment reduces metabolic syndrome-related diabetic cardiomyopathy," *European Heart Journal* 38(Suppl_1):ehx501.P577, Oxford University Press, United Kingdom (Aug. 2017).

Lam, C.S.P., et al., "Epidemiology and clinical course of heart failure with preserved ejection fraction," *Eur. J. Heart Failure* 13(1):18-28, Wiley-Blackwell, United States (2011).

Lloyd-Jones, D.M., et al., "Defining and setting national goals for cardiovascular health promotion and disease reduction: the American Heart Association's strategic Impact Goal through 2020 and beyond," *Circulation* 121(4):586-613, Lippincott Williams and Wilkins Ltd., United States (2010).

Marin-Penalver, J.J., et al., "Update on the treatment of type 2 diabetes mellitus," *World J. Diabetes* 7(17):354-95, Baishideng Publishing Group, United States (2016).

Matter, C.M., et al., "Effect of No Donors on LV Diastolic Function in Patients With Severe Pressure-Overload Hypertrophy," *Circulation* 99(18):2396-2401, Lippincott Williams and Wilkins Ltd., United States (1999).

Merabet, N., et al., "Soluble epoxide hydrolase inhibition improves myocardial perfusion and function in experimental heart failure," *Journal of Molecular and Cellular Cardiology* 52(3):660-666, Academic Press Inc., United States (2012).

Mulder, P., et al., "Increased Survival After Long-Term Treatment With Mibefradil, a Selective T-Channel Calcium Antagonist, in Heart Failure," *Journal of the American College of Cardiology* 29(2):416-421, Elsevier, Netherlands (1997).

Mulder, P., et al., "Aldosterone synthase inhibition improves cardiovascular function and structure in rats with heart failure: a comparison with spironolactone," *Eur Heart J* 29(17):2171-2179, Oxford University Press, United Kingdom (2008).

Oghlakian, G.O., et al., "Treatment of Heart Failure With Preserved Ejection Fraction: Have We Been Pursuing the Wrong Paradigm?" *Mayo Clinic Proceedings* 86(6):531-539, Elsevier Science, Netherlands (2011).

Owan, T.E., et al., "Epidemiology of diastolic heart failure," *Prog Cardiofasc Dis* 47(5):320-332, W.B. Saunders Ltd., United Kingdom (2005).

Palsson, R., et al., "Cardiovascular complications of diabetic kidney disease," *Adv. Chronic. Kidney Dis.* 21(3):273-80, Elsevier, Netherlands (2014).

Pirags, V., et al., "Imeglimin, a novel glimin oral antidiabetic, exhibits a good efficacy and safety profile in type 2 diabetic patients," *Diabetes, Obesity and Metabolism* 14(9):852-8, Wiley-Blackwell Publishing Ltd., United Kingdom (2012).

Pirags, V. et al., "Imeglimin, a novel glimin oral anti-diabetic, exhibits good glycemic control in Type 2 diabetic patients," Poster Presentation, 1 page, Poxel, France (2010).

"Poxel Corporate Presentation," "Imeglimin" and "PXL770," presented by Poxel in Jan. 2017, 39 pages.

Poxel, Press Release on Jun. 6, 2017, "Poxel Announces Additional Positive Results for Imeglimin Phase 2b Study in Japan for the Treatment of Type 2 Diabetes," accessed at https://www.poxelpharma.com/en_us/investors/news-events/press-releases/detail/62/poxel-announces-additional-positive-results-for-imeglimin on Sep. 18, 2020, 4 pages.

Redfield, M.M., et al., "Burden of systolic and diastolic ventricular dysfunction in the community: appreciating the scope of the heart failure epidemic," *JAMA* 289(2):194-202, American Medical Association, United States (2003).

Sakamoto, M., et al., "Possibility of a New Therapeutic Strategy for Left Ventricular Dysfunction in Type 2 Diabetes," *Journal of Clinical Medicine Research* 10(11):799-805, Elmer Press Inc., Canada (Nov. 2018).

Silberman, G.A., et al., "Uncoupled cardiac nitric oxide synthase mediates diastolic dysfunction," *Circulation* 121(4):519-528, Lippincott Williams and Wilkins Ltd., United States (2010).

Tuttle, K.R., et al., "Diabetic Kidney Disease: A Report From an ADA Consensus Conference," *Diabetes Care* 37(10): 2864-2883, American Diabetes Association, United States (2014).

Van Heerebeek, L., et al., "Diastolic stiffness of the failing diabetic heart: importance of fibrosis, advanced glycation end products, and myocyte resting tension," *Circulation* 117(1):43-51, Lippincott Williams and Wilkins Ltd., United States (2008).

Van Heerebeek, L., et al., "The failing diabetic heart: focus on diastolic left ventricular dysfunction," *Curr Diab Rep* 9(1):79-86, Current Medicine Group, United States (2009).

Vercauteren, M., et al., "Improvement of Peripheral Endothelial Dysfunction by Protein Tyrosine Phosphatase Inhibitors in Heart Failure," *Circulation* 114:2498-2507, Lippincott Williams and Wilkins Ltd., United States (2006).

Vuylsteke, V., et al., "Imeglimin: A potential new mutli-target drug for type 2 diabetes," *Drugs in R and D* 75(3): 227-32, Adis International Ltd., United Kingdom (2015).

Yancy, C.W., et al., "Clinical presentation, management, and in-hospital outcomes of patients admitted with acute decompensated heart failure with preserved systolic function: a report from the Acute Decompensated Heart Failure National Registry (ADHERE) Database," *J Am College Cardiol* 47(1):76-84, Elsevier, Netherlands (2006).

Marianne Lachaux et al., "Short and long-term imeglimin treatment reduces metabolic syndrome-related diabetic cardiomyopathy", Inserm, poster presentation at European Association for the Study of Diabetes, Aug. 2017.

* cited by examiner

METHODS OF TREATING HEART FAILURE WITH PRESERVED EJECTION FRACTION

FIELD OF THE INVENTION

The present invention relates to the field of medicine, in particular of cardiology. It provides new treatments for hearth failure with preserved ejection fraction.

BACKGROUND OF THE INVENTION

Heart failure (HF) is the leading cause of cardiovascular morbidity and mortality worldwide. It affects about 2% of the western population and 10% of adults aged over 75 years (Lam et al., 2011, Eur. J. Heart Failure 13:18-28). Heart failure is the most common cause of hospitalization in adults over 65 years of age (Lam et al).

HF can be classified according to different criteria such as the side of the heart affected, the severity of the disease, the heart function affected or the phase of the cardiac cycle which is impaired. The cardiac cycle comprises two main phases, the systole and the diastole. Systole is the phase of the cardiac cycle in which the heart is contracting to propel blood out to the body, brain and lungs, whereas diastole is the phase of the cardiac cycle in which the heart is relaxing and filling with incoming blood that is being returned from the body through the inferior vena cava (IVC) and through the superior vena cava (SVC). The better defined type of heart failure is associated with an impairment of the systolic phase. In such a heart failure, the ventricle cannot contract properly which leads to a reduction of the ejection fraction. This type of heart failure is called Heart Failure with Reduced Ejection Fraction (HFREF). Another type of heart failure has been associated with impairment of the diastolic phase. In such a heart failure, the ejection fraction is preserved (Heart Failure with Preserved Ejection Fraction or HFPEF). HFPEF is associated with a decline in diastolic performances of the left ventricle of the heart. Indeed, when the cardiac muscle becomes stiff and loses its ability to relax, the left ventricle cannot readily fill with blood following contraction and the cardiac output either diminishes or remains normal as a result of an elevated ventricular filling pressure. The HFPEF is often characterized histologically by a hypertrophy of cardiomyocytes and increased interstitial collagen deposition and calcium deposition within the myocardium which are assumed to lead collectively to decreased distensibility and LV compliance.

About half of heart failure patients suffer from HFPEF. Indeed, approximately 54% of patients with heart failure (Lam et al; Redfield et al, 2003, Jama 289:194-202; Kitzman et al, 2001, Am. J. Cardiol. 87:413-419; Devereux et al., 2000. Am. J. Cardiol. 86:1090-1096; Ceia et al., 2002, Eur. J. Herat Failure 4:531-539) and 46-51% of patients hospitalized for acute heart failure have HFPEF (Lam et al; Fonarow et al., 2007, J. Am. College Cardiol. 50:768-777; Yancy et al., 2006, J. Am. College Cardiol. 47:76-84).

Each year, the number of new cases of heart failure is increasing. Indeed, the number of new heart failure cases in the US has increased from 48,000 in 2000 to 670,000 in 2007 (Lam et al; Lloyd-Jones et al., 2010, Circulation 121:586-613), greatly exceeding previous forecasts and suggesting that a further dramatic increase should be expected in the next few decades. Assuming that half the caseload of heart failure consists of HFPEF, an equal increase in HFPEF burden can be projected. Even these may be conservative estimates, since the relative prevalence of HFPEF, as a proportion of the total burden of heart failure cases, is increasing as the population ages (Lam et al; Owan et al., 2005, Prog. Cardiofasc. Dis. 47:320-332), and the survival in patients with HFREF is improving but not in those with HFPEF. Therefore, although already an epidemic, a further dramatic increase in the prevalence of HFPEF is anticipated (Lam et al).

Multiple therapies that provide substantial clinical benefit in HFREF are nowadays available. However, these therapies are not effective in treating or preventing HFPEF (From et al., Cardiovascular Therapeutics, 2011, 29:e6-21). There are currently no effective dietary or pharmacological interventions that improve long-term outcomes in patients with HFPEF (Oghlakian et al., 2011, Mayo Clin Proc. 86:531-539; Komajda M. et al, 2014, Eur. Heart J, 35: 1022-1032). When the chronic condition is tolerable by the patient, the therapy is only directed to alleviating aggravating factors such as high blood pressure. There is thus a strong need for the development of new methods of treating HFPEF. The present invention seeks to meet these and other needs.

SUMMARY OF THE INVENTION

The inventors have surprisingly found that Imeglimin. a triazine derivative, is very effective in treating HFPEF. Indeed, in a model of Zucker fa/fa Rats, a model of metabolic syndrome used for the evaluation of cardiac diastolic dysfunction and in particular HFPEF, the inventors have observed that rats present a great improvement of their diastolic parameters when treated with imeglimin. They particularly noticed a significant reduction of the left ventricular end-diastolic pressure-volume relation in Zucker fa/fa rats after 9 and 90 days of treatment. The left ventricular end-diastolic pressure-volume relation is an index of diastolic dysfunction and left ventricular stiffness and in particular of HFPEF. The reduction of the left ventricular end-diastolic pressure-volume relation was even of about 26% and 58% after 9 and 90 days of treatment of the Zucker fa/fa rats with imeglimin respectively.

Accordingly, in a first aspect, the present invention concerns a method for treating HFPEF, wherein the method comprises administering to a patient having or at risk of developing HFPEF a therapeutically effective amount of imeglimin.

The invention also concerns, in a second aspect, a method for treating HFPEF, wherein the method comprises administering to a patient having or at risk of developing HFPEF a pharmaceutical composition comprising a therapeutically effective amount of imeglimin and at least one pharmaceutically acceptable carrier.

Preferably, the patient to be treated is a human, more preferably an adult human, preferably of at least 50 years old, more preferably of at least 60 years old, even more preferably of at least 75 years old.

Preferably, the ejection fraction of the patient is superior or equal to 45%, more preferably to 50%, even more preferably to 55%.

Preferably, imeglimin is administered to the patient at a concentration comprised between about 10 mg/kg of body weight/day and about 100 mg/kg of body weight/day, preferably between about 15 mg/kg of body weight/day and about 60 mg/kg of body weight/day, preferably between about 20 mg/kg of body weight/day and about 50 mg/kg of body weight/day, more preferably between about 30 mg/kg of body weight/day and about 45 mg/kg of body weight/day.

Preferably the patient suffers from a metabolic syndrome, preferably selected from the group consisting of obesity and diabetes, in particular type 2 diabetes, monogenic diabetes mellitus, and transient neonatal hyperglycemia.

BRIEF DESCRIPTION OF THE DRAWINGS

FIGS. 1A and 1B: Imeglimin Treatment Improves Left Ventricle Diastolic Dysfunction in Zucker Fa/Fa Rats

\*: $p<0.05$ vs lean; †: $p<0.05$ vs Zucker with vehicle

FIGS. 2A and 2B: Imeglimin Treatment Improves Cardiac Output and Myocardial Perfusion in Zucker Fa/Fa Rats

\*: $p<0.05$ vs lean; †: $p<0.05$ vs Zucker with vehicle

FIG. 3: Imeglimin Treatment Prevents the Impairment in Acetylcholine-Induced Relaxation of Septal Coronary Artery of Zucker Fa/Fa Rats

\*$p<0.05$ vs lean rats; †: $p<0.05$ vs Zucker with vehicle

DETAILED DESCRIPTION OF THE INVENTION

The inventors have surprisingly found that imeglimin is very effective in treating HFPEF. Indeed, in a model of Zucker fa/fa rats, a model of metabolic syndrome used for the evaluation of HFPEF, such rats present a great improvement of their diastolic parameters when treated with imeglimin. The inventors particularly noticed an important reduction of the left ventricular end-diastolic pressure-volume relation in Zucker fa/fa rats after imeglimin treatment. The left ventricular end-diastolic pressure-volume relation is an index of LV compliance, a key factor in HFPEF.

Definitions

As used herein, the terms "Heart failure (HF)", "congestive heart failure", "chronic heart failure", and "acute heart failure" are used interchangeably, and refer to any condition in which the heart is unable to pump blood at an adequate rate or is able to do so only in the presence of increased left ventricular filling pressures. As used herein the term "adequate rate" refers to a rate allowing to supply sufficient blood to meet the needs of the body. When the heart is unable to adequately pump blood to the rest of the body at normal filling left ventricular pressures, blood can back up into the lungs, causing the lungs to become congested with fluid. Typical symptoms of heart failure include shortness of breath (dyspnea), fatigue, weakness, difficulty of breathing when lying flat, and swelling of the legs, ankles or abdomen (edema). Causes of heart failure are related to various disorders including coronary arterial disease, systemic hypertension, cardiomyopathy or myocarditis, congenital heart disease, abnormal heart valves or valvular heart disease, severe lung disease, diabetes, severe anemia hyperthyroidism, arrhythmia or dysrhythmia and myocardial infarction.

Heart failure can occur in the presence of a normal or a reduced left ventricular ejection fraction. As used herein, the terms "Heart Failure with Preserved Ejection Fraction", "heart failure with normal ejection fraction" or "diastolic heart failure (DHF)", are equivalent and refer to a patient that suffers from heart failure and that does not present a significant reduction of its left ventricular ejection fraction compared to that of a control (e.g., a healthy individual) or compared to an average value from a healthy population. In certain embodiments, an ejection fraction is classified as normal and a patient suffering from HF is classified as having a HFPEF when the ejection fraction is superior or equal to 40%, preferably superior or equal to 45%, more preferably superior or equal to 50%, still more preferably superior or equal to 55%, yet more preferably superior or equal to 60%. HFPEF usually occurs in older patients with risk factors such as obesity, diabetes and hypertension and is more common in women.

The term "Ejection Fraction", as used herein, refers to the division of the left ventricle stroke volume by its end-diastolic volume. In other words, the term "ejection fraction" refers to the percentage of blood that is pumped out of a filled ventricle with each heartbeat. Methods for measuring the ejection fraction, for example with an echocardiogram, are well known by a person skilled in the art.

As used herein, the terms "subject", "individual" or "patient" are interchangeable and refer to an animal, preferably to a mammal, even more preferably to a human. However, the term "subject" can also refer to non-human animals, in particular mammals such as dogs, cats, horses, cows, pigs, sheep and non-human primates, among others.

As used herein, the term "treatment", "treat" or "treating" refers to any act intended to ameliorate the health status of patients such as therapy, retardation, delaying the worsening of a disease or disorder. In certain embodiments, such term refers to the amelioration or eradication of a disease or disorder or symptoms associated with said disease or disorder. In other embodiments, this term refers to minimizing the worsening of the disease or disorder resulting from the administration of one or more therapeutic agents to a subject with such a disease or disorder. In a preferred embodiment, the disease or disorder is HFPEF.

As used herein, the terms "prevent," "preventing," and "prevention" refer to a method of preventing the onset of a disease or condition and/or its attendant symptoms or barring a subject from acquiring a disease. As used herein, "prevent," "preventing," and "prevention" also include delaying the onset of a disease and/or its attendant symptoms and reducing a subject's risk of acquiring a disease. The terms "prevent," "preventing" and "prevention" may include "prophylactic treatment," which refers to reducing the probability of redeveloping a disease or condition, or of a recurrence of a previously-controlled disease or condition, in a subject who does not have, but is at risk of or is susceptible to, redeveloping a disease or condition or a recurrence of the disease or condition.

As used herein, the term "disease" refers to a state of health of a subject wherein the subject cannot maintain homeostasis, and wherein if the disease is not ameliorated then the subject's health continues to deteriorate.

As used herein, the term "disorder" refers to a state of health of a subject in which the subject is able to maintain homeostasis but in which the subject's state of health is less favourable than it would be in the absence of the disorder. Left untreated, a disorder does not necessarily cause a further decrease in the subject's state of health.

As used herein, the terms "active principle", "active ingredient" "active pharmaceutical ingredient", and "therapeutic agent" are equivalent and refer to a component having a therapeutic effect.

As used herein, the term "therapeutic effect" refers to an effect induced by an active ingredient or by a pharmaceutical composition according to the invention, capable to prevent or to delay the onset or the development of HFPEF, or to cure or to attenuate the effects of HFPEF.

As used herein, the term "excipient or pharmaceutically acceptable carrier" refers to any ingredient except active ingredients that is present in a pharmaceutical composition. Its addition may be aimed at conferring a particular consistency or other physical or gustative properties to the final product.

The terms "quantity," "amount," and "level" are used interchangeably herein and refer to an absolute quantification of a molecule or ingredient. As used herein, the term "effective amount" refers to a quantity of an active ingredient that is sufficient or effective to prevent, remove or reduce the deleterious effects of a disease or disorder related to HFPEF. The quantity to be administered can be adapted by the person skilled in the art according to the subject to be treated, to the symptoms of the HFPEF, etc. In particular, doses and regimen of administration may be a function of the nature, the stage and the severity of the HFPEF to be treated, as well as the weight, the age and the global health of the subject to be treated, as well as the judgment of the doctor.

As used herein, the term "diagnosis" refers to the determination as to whether a subject is likely to be affected with HFPEF.

The term "about" refers to a range of values of ±10% of the specified value. For example, "about 50" comprises values of ±10% of 50, i.e. values in the range between 45 and 55. Preferably, the term "about" refers to a range of values of ±5% of the specified value.

In a first aspect, the present invention concerns a method for treating HFPEF, wherein the method comprises administering to a patient having HFPEF a therapeutically effective amount of imeglimin.

In a second aspect, the invention also concerns a method for treating HFPEF, wherein the method comprises administering to a patient having HFPEF a pharmaceutical composition comprising therapeutically effective amount of imeglimin. In some embodiments, the invention concerns a method for treating HFPEF, wherein the method comprises administering to a patient having HFPEF a pharmaceutical composition comprising therapeutically effective amount of imeglimin as the sole active ingredient. Preferably the pharmaceutical composition further comprises at least one pharmaceutically acceptable carrier.

HFPEF Patient

The methods according to the invention are aimed to treat a patient affected with HFPEF.

The patient is an animal, preferably a mammal, even more preferably a human. However, the patient can also be a non-human animal, in particular mammals such as dogs, cats, horses, cows, pigs, sheep, donkeys, rabbits, ferrets, gerbils, hamsters, chinchillas, rats, mice, guinea pigs and non-human primates, among others, that are in need of treatment.

The human patient according to the invention may be a child, an infant, an adolescent or an adult, preferably an adult.

The human patient according to the invention is preferably an adult of at least 40 years old, more preferably an adult of at least 50 years old, still more preferably an adult of at least 60 years old, yet more preferably an adult of at least 65 years old, even more preferably an adult of at least 70 years old. In a most preferred embodiment, the human patient according to the invention is an adult of at least 75 years old. In some embodiments, the adult is about 40 years old or older, the adult is about 50 years old or older, the adult is about 60 years old or older, the adult is about 65 years old or older, the adult is about 70 years old or older, or the adult is about 75 years old or older.

Preferably, the patient is a women.

Preferably, the patient has been diagnosed with HFPEF.

In a first embodiment, a patient is considered as being affected with HFPEF when he suffers from heart failure and presents a preserved ejection fraction, in particular he does not present a significant reduction of its left ventricular ejection fraction compared to that of a control (e.g., a healthy individual) or compared to an average value from a healthy population. Preferably, the ejection fraction of the patient suffering from HFPEF is superior or equal to about 40%, preferably superior or equal to about 45%, more preferably superior or equal to about 50%. Alternatively, the ejection fraction of the patient suffering from HFPEF is superior or equal to about 55%, preferably superior or equal to about 60%.

In another embodiment, a patient may be considered as being affected with HFPEF when he presents an elevated B-type natriuretic peptide (BNP) level in combination with a normal ejection fraction. Preferably, a patient has an elevated BNP level when he presents a BNP blood concentration superior to about 35 pg/ml, preferably superior to about 50 pg/ml, more preferably superior to about 75 pg/ml, still more preferably superior to about 100 pg/ml, even more preferably superior to about 200 pg/ml.

Echocardiography techniques can be used to diagnose diastolic dysfunction and require measurement of multiple echocardiographic parameters to confirm an HFPEF diagnosis. So a combined approach is needed. Multiple echocardiographic parameters have been proposed as sensitive and specific, including mitral inflow velocity patterns, pulmonary vein flow patterns, E:A reversal, tissue Doppler measurements (i.e., E/E' ratio), and M-mode echo measurements (i.e. of left atrial size). Algorithms have further been developed which combine multiple echocardiographic parameters. A person skilled in the art is able to choose the most appropriate parameters and/or algorithms.

There are four basic echocardiographic patterns of diastolic dysfunction, which are graded from I to IV:

the mildest form is called an "abnormal relaxation pattern", or grade I diastolic dysfunction. On the mitral inflow Doppler echocardiogram, there is reversal of the normal E/A ratio. This pattern may develop normally with age in some patients, and many grade I patients will not have any clinical signs or symptoms of heart failure;

grade II diastolic dysfunction is called "pseudo normal filling dynamics". This is considered moderate diastolic dysfunction and is associated with elevated left atrial filling pressures. These patients more commonly have symptoms of heart failure, and many have left atrial enlargement due to the elevated pressures in the left heart:

grades III and IV diastolic dysfunction are called "restrictive filling dynamics". These are both severe forms of diastolic dysfunction, and patients tend to have advanced heart failure symptoms:

grade III diastolic dysfunction patients will demonstrate reversal of their diastolic abnormalities on echocardiogram when they perform the Valsalva maneuver. This is referred to as "reversible restrictive diastolic dysfunction";

grade IV diastolic dysfunction patients will not demonstrate reversibility of their echocardiogram abnormalities, and are therefore said to suffer from "fixed, restrictive diastolic dysfunction".

The presence of either grade III or IV diastolic dysfunction is associated with a significantly bad prognosis. These patients will have left atrial enlargement.

Accordingly, in a particular embodiment, a patient may be considered as being affected with HFPEF when he presents a heart failure and a diastolic dysfunction, preferably of at least grade I, more preferably of at least grade II, even more preferably of at least grade III. In a most preferred embodiment, a patient is considered as being affected with HFPEF when he presents a heart failure and a diastolic dysfunction of grade IV.

In a particular embodiment, a patient is considered as being affected with HFPEF if:

a) the patient presents one or several heart failure typical symptoms, preferably at least 2 heart failure typical symptoms, more preferably at least 3 heart failure typical symptoms, still more preferably at least 4 heart failure typical symptoms, yet more preferably at least 6 heart failure typical symptoms, even more preferably at least 8 heart failure typical symptoms, said symptoms being preferably selected from the group consisting of shortness of breath or dyspnea, in particular a dyspnea of isolated effort, fatigue, feeling lightheaded, difficulty breathing when lying flat, chronic coughing or wheezing, swelling of the legs, ankles or abdomen (edema), nausea, lack of appetite, confusion or impaired thinking, and high heart rate; preferably the patient presents all these symptoms; and b) an ejection fraction superior or equal to about 40%, preferably superior or equal to about 45%, more preferably superior or equal to about 50%, still more preferably superior or equal to about 55%, yet more preferably superior or equal to about 60%; and c) optionally, in particular when the ejection fraction is comprised between about 40% and 50%, a normal end-diastolic volume, preferably inferior to 97 ml/m$^2$, more preferably comprised between 50 ml/m$^2$ and 97 ml/m$^2$; and d) optionally, in particular when the ejection fraction is comprised between about 40% and 50%, a diastolic function anomaly, preferably evidenced by abnormal echocardiographic parameter(s):

an E/E'>8, preferably an E/E'>12, even more preferably an EE'>13; and optionally, in particular when 8<E/E'<12, one of the following parameters, preferably two of the following parameters, more preferably all of the following parameters:

concerning the pulmonary vein flow, an Ap-Am>20 ms, preferably an Ap-Am>30 ms; and a dilated left auricle, preferably superior to 40 ml/m$^2$; and a left ventricular hypertrophy, preferably with a left ventricular mass index superior to 149 g/m$^2$ for men and superior to 122 g/m$^2$ for women; and an E/A<0.5 and a TDM>280 ms; and an auricle fibrillation; or optionally, in particular when 8<E/E'<12, a BNP blood concentration superior to 35 pg/ml, preferably superior to 50 pg/ml, more preferably superior to 75 pg/ml, still more preferably superior to 100 pg/ml, even more preferably superior to 200 pg/ml.

Preferably, the patient further suffers from a metabolic syndrome such as obesity or diabetes, in particular type 2 diabetes, monogenic diabetes mellitus, and transient neonatal hyperglycemia. In some embodiments, the patient further suffers from type 2 diabetes.

Preferably, the patient further suffers from hypertension, elevated fasting plasma glucose, high serum triglycerides, low high-density lipoprotein (HDL) levels, or a mixture thereof. The patient can also further suffer from coronary artery disease, systemic hypertension, cardiomyopathy or myocarditis, congenital heart disease, abnormal heart valves or valvular heart disease, severe lung disease, severe anemia hyperthyroidism, arrhythmia or dysrhythmia and myocardial infarction.

Preferably, the patient further suffers from endothelial dysfunction

Preferably, the patient has already received a heart failure treatment.

In a particular embodiment, the patient does not have HFPEF but is at risk of developing HFPEF. A patient at risk of developing HFPEF does not necessarily suffer from heart failure. However, he can still present one or several of the heart failure symptoms.

A patient at risk of developing HFPEF can be, for example, a patient presenting a diastolic dysfunction of grade I or II as defined above, preferably of grade I, and who does not suffer from heart failure.

A patient at risk of developing HFPEF can also be, for example, a patient who presents some symptoms of heart failure as described above, preferably no more than 2 heart failure symptom, including but not limited to shortness of breath, leg swelling, and exercise intolerance, and/or one or more other risk factors, including but not limited to:

a genetic predisposition to HFPEF;
a family member with HFPEF;
a myocardial infarction;
a cardiomyopathy;
a ventricular diastolic dysfunction;
a ventricular systolic dysfunction;
a ventricular systolic stiffening;
a vascular stiffening and dysfunction;
an endothelial dysfunction;
a left atrial dysfunction;
a pulmonary hypertension;
an autonomic dysfunction (e.g. chronotropic incompetence; sympathetic hyperactivation);
a skeletal muscle dysfunction (e.g. impaired vasodilation; sympathetic hyperactivation and ergoreflex stimulation); or anemia.

Accordingly, in a particular aspect, the invention also concerns a method for preventing HFPEF, wherein the method comprises administering to a patient at risk of developing HFPEF a therapeutically effective amount of imeglimin.

In another particular aspect, the invention also concerns a method for preventing HFPEF, wherein the method comprise administering to a patient at risk of developing HFPEF a therapeutically effective amount of a pharmaceutical composition comprising a therapeutically effective amount of imeglimin. In another aspect, the invention concerns a method for preventing HFPEF, wherein the method comprise of administering to a patient at risk of developing HFPEF a therapeutically effective amount of a pharmaceutical composition comprising a therapeutically effective amount of imeglimin as the sole active ingredient. Preferably the pharmaceutical composition further comprises at least one pharmaceutically acceptable carrier.

Imeglimin, Pharmaceutical Composition, Dose, Regimen and Administration

The methods according to the invention comprise administering a therapeutically effective amount of imeglimin or a pharmaceutical composition comprising a therapeutically effective amount of imeglimin to the patient.

Imeglimin is a triazine derivative (a tetrahydrothiazine) belonging to the chemical class of the glimins and corresponding to (+)-2-amino-3,6-dihydro-4-dimethylamino-6-methyl-1,3,5-triazine or (6R)-(+)-4-dimethylamino-2-imino-6-methyl-1,2,5,6-tetrahydro-1,3,5 triazine, which may for instance be synthetized as described in WO 2009/095159, WO 2012/072663, WO 2010/012746, WO 2009/141040, or a combination thereof. Imeglimin is also described in U.S. Pat. Nos. 7,034,021, 7,452,883, 7,767,676, 7,501,511, 8,227,465, 8,791,115, 8,217,040, 8,461,331, 8,846,911, 9,035,048, 8,742,102, 8,592,370, 8,980,828, 8,742,103, 9,271,984, and 8,937,066.

In some embodiments, imeglimin is administered in the form of a hydrochloride salt. As described herein, the amount of the imeglimin administered to a subject refers to the amount of the imeglimin free base. The embodiments described herein may refer to "imeglimin" when imeglimin hydrochloride is used.

Preferably, the pharmaceutical composition comprises at least one excipient or pharmaceutically acceptable carrier. Conventional excipients can be used according to techniques well known by those skilled in the art. The pharmaceutical composition comprising imeglimin is formulated in accordance with standard pharmaceutical practice (Lippincott Williams & Wilkins, 2000 and Encyclopedia of Pharmaceutical Technology, eds. J. Swarbrick and J. C. Boylan, 1988-1999, Marcel Dekker, New York) known by a person skilled in the art.

Preferably, the treatment with imeglimin or the pharmaceutical composition according to the invention starts no longer than a month, preferably no longer than a week, after the HFPEF has been diagnosed. In a most preferred embodiment, the treatment starts the day of the diagnosis or the day after the diagnosis.

The treatment with imeglimin or the pharmaceutical composition according to the invention may be administered as a single dose or in multiple doses, preferably in multiple doses.

Preferably, the treatment is administered regularly, preferably between every day and every week, more preferably every day. In one embodiment, the treatment is administered once a day. In a particular embodiment, the treatment is administered several times a day, preferably 2 or 3 times a day, even more preferably 2 times a day.

The duration of treatment with imeglimin or the pharmaceutical composition according to the invention is preferably comprised between 1 day and 50 weeks, more preferably between 1 day and 24 weeks. In a particular embodiment, the treatment lasts as long as the HFPEF persists. In a most preferred embodiment, the treatment is a life treatment.

The amount of imeglimin to be administered has to be determined by standard procedure well known by those of ordinary skills in the art. Physiological data of the patient (e.g. age, size, weight, and physical general condition) and the routes of administration have to be taken into account to determine the appropriate dosage, so a therapeutically effective amount will be administered to the patient.

In a preferred embodiment, the total imeglimin dose administered per day of treatment with imeglimin or with the pharmaceutical composition according to the invention is comprised between about 500 mg and about 5000 mg, preferably between about 1000 and about 4000, more preferably between about 1500 mg and about 3500 mg, even more preferably between about 2000 mg and about 3000 mg.

In another preferred embodiment, imeglimin is administered to the patient at an amount comprised between about 10 mg/kg of body weight/day and about 100 mg/kg of body weight/day, preferably between about 15 mg/kg of body weight/day and about 60 mg/kg of body weight/day, preferably between about 20 mg/kg of body weight/day and about 50 mg/kg of body weight/day, more preferably between about 30 mg/kg of body weight/day and about 45 mg/kg of body weight/day.

In one embodiment, imeglimin is administered to the patient at a daily dose of about 500 mg, about 1000 mg, about 1500 mg, about 2000 mg, about 2500 mg, about 3000 mg, about 3500 mg, about 4000 mg, about 4500 mg, about 5000 mg, or in a range between any two of the preceding values.

In one embodiment, imeglimin is administered to the patient at a daily dose of 1000 mg, 1500 mg, 2000 mg, 2500 mg, or 3000 mg.

Imeglimin or the pharmaceutical composition according to the invention can be administered by any conventional route of administration, such as topical, enteral, in particular oral or rectal, parenteral, in particular intravenous, intranasal, intramuscular, cutaneous, subcutaneous, or intraocular route of administration and the like.

Preferably, imeglimin or the pharmaceutical composition according to the invention may be administered by enteral or parenteral route of administration. When administered parenterally, the imeglimin or the pharmaceutical composition according to the invention is preferably administered by intravenous route of administration. When administered enterally, imeglimin or the pharmaceutical composition according to the invention is preferably administered by oral route of administration. In a most preferred embodiment, imeglimin is administered orally.

For oral administration, the pharmaceutical composition can be formulated into conventional oral dosage forms such as tablets, capsules, powders, granules, gel capsules, and liquid preparations such as syrups, elixirs, solutions, emulsions, suspensions, and concentrated drops. Nontoxic solid carriers or diluents can be used for oral administration. In some embodiments, imeglimin is administered as tablets.

For compressed tablets, binders, which are agents which impart cohesive qualities to powdered materials, are also necessary. Disintegrants are also usually necessary in tablets to facilitate break-up of the tablet. Moreover, lubricants and glidants can also be included in the tablets to prevent adhesion of the tablet material to surfaces in the manufacturing process and to improve the flow characteristics of the powder material during manufacture. If necessary, the tablet can be coated via the known techniques, in order to mask the taste or to allow enteric dissolution or sustained release of the active principles.

Liquid pharmaceutical forms for oral administration include solutions, suspensions and emulsions. The aqueous solutions can be obtained by dissolving the active principle in water, followed by addition of flavourings, colorants, stabilisers and/or thickeners, if necessary. In order to improve the solubility, a pharmaceutically acceptable non-aqueous solvent can be added. The aqueous suspensions for oral use can be obtained by dispersing the finely divided active principle in water with a viscous product.

The pharmaceutical forms for injection can be obtained, for example, by the following process. The active principle is dissolved, suspended or emulsified either in an aqueous medium or in an oily medium, with a dispersant, a preserving agent, an isotonicity agent, and optionally other additives, such as, if desired, a solubilising agent or a stabiliser.

Pharmaceutical forms for external use can be obtained from a solid, semi-solid or liquid composition containing the active principle. For example, to obtain a solid form, the active principle can be treated with excipients and a thickener so as to convert them into powder. The liquid pharmaceutical compositions are prepared in substantially the same way as the forms for injection, as indicated previously. The semi-solid pharmaceutical forms are preferably in the form of aqueous or oily gels or in the form of pomades. These compositions may optionally contain a pH regulator and a preserving agent.

For transdermal administration, the pharmaceutical composition can be formulated into ointment, cream or gel form and appropriate penetrants or detergents could be used to facilitate permeation.

For transmucosal administration, nasal sprays, rectal or vaginal suppositories can be used. The active compound can be incorporated into any of the known suppository bases.

Pharmaceutical compositions according to the invention may be formulated to release the active drug substantially immediately upon administration or at any predetermined time or time period after administration.

The pharmaceutical composition of the invention may be administered to a patient by sustained release. Sustained release administration is a method of drug delivery to achieve a certain level of the drug over a particular period of time.

In a particular embodiment, the treatment with imeglimin or with the pharmaceutical composition according to the invention is used in conjunction with physical exercise, in particular aerobic exercise training, preferably aerobic exercise training on peak oxygen consumption, and/or with a specific diet, in particular a caloric restriction diet and/or a high nitrate diet.

In some embodiments, imeglimin is administered with a second pharmaceutical agent. In some embodiments, imeglimin is administered concomitantly with the second pharmaceutical agent. In some embodiments, imeglimin is administered sequentially with the second pharmaceutical agent. The second pharmaceutical agent can be a drug for treating heart failure with reduced ejection fraction, including but not limited to ACE inhibitors, Angiotensin II Receptor Blockers, $I_f$ Channel Blocker, Diuretics, aldosterone antagonists, beta blockers, statins, and acetylsalicylic acid. The second pharmaceutical agent can also be an antidiabetic drug if the patient suffers from type 2 diabetes. In some embodiments the second pharmaceutical agent is selected from the group consisting of an insulin, an alpha-glucosidase inhibitor, a biguanide, a dopamine agonist, a DPP-4 inhibitor, a glucagon-like peptide, a meglitinide, a sodium glucose transporter (SGLT2 or SGLT1/2) inhibitor, a sulfonylurea, a thiazolidinedione, and a combination thereof.

The form of the pharmaceutical compositions, the route of administration and the dose of administration of imeglimin or of the pharmaceutical composition according to the invention can be adjusted by a person skilled in the art according to the type and severity of the disease, and the patient, in particular its age, weight, sex, and general physical condition.

All the references cited in this application, including scientific articles and summaries, published patent applications, granted patents or any other references, are entirely incorporated herein by reference, which includes all the results, tables, figures and texts of theses references.

Although having different meanings, the terms "comprising", "having", and "containing" can be replaced one for the other in the entire application.

Further aspects and advantages of the present invention will be described in the following examples, which should be regarded as illustrative and not limiting.

Examples

Materials and Methods
Animals and Treatment

Experiments were performed on 12-week-old Male Zucker fa/fa rats or lean control rats purchased from Ch. River (US).

Animals were kept 2 per cage in standard laboratory conditions, and drugs were administered by gavage (at 9 am and at 6 pm) at the dose of 150 mg/kg bid and administered for 9 or 90 days. Imeglimin's effects on cardiac dysfunction were assessed.

First experiment protocol:

The Zucker fa/fa animals were randomized on their body weight in two groups and three groups were then constituted:
 Lean rats (Treated with vehicle n=12)
 Control Zucker fa/fa rats (Treated with vehicle n=18)
 Imeglimin treated Zucker fa/fa rats at the dose of 150 mg/kg bid (n=18)

After a short-term treatment (9 days), cardiac function (echocardiography and MRI) and cardiac hemodynamics were assessed (1 h after the last treatment) on all rats.

Second experiment protocol:

The Zucker fa/fa animals were randomized on their body weight in two groups and three groups were then constituted:
 Lean rats (Treated with vehicle n=18)
 Control Zucker fa/fa rats (Treated with vehicle n=24)
 Imeglimin treated Zucker fa/fa rats at the dose of 150 mg/kg bid (n=24)

After a long-term treatment (90 days), cardiac function (echocardiography and MRI) and cardiac hemodynamics were assessed (1 h after the last treatment) on all rats.

Preparation of the Vehicle and Drug Suspension

Vehicle: 5 g of Methylcellulose were weighed and completely homogenized by stirring in 1 liter of distilled water (during 18 h to 24 h). The stock solution was stored at 4° C.

The imeglimin suspension was prepared at the concentrations used in the study (150 mg/kg) and homogenized in 10 mL of the Methylcellulose solution. The drug suspension was prepared on the day of administration.

Body Weight and Food Intake

Body weight was measured once a week for adjustment of imeglimin treatment concentration.

Echocardiography

Studies were performed on rats after 9 and 90 days of treatment. For this purpose, rats were anesthetized with methohexital, the chest shaved and echocardiograms performed with a Vivid 7 ultrasound echograph equipped with a M12L linear probe operating at 14 MHz and fitted out with Echopac PC software (GE medical) as described previously (Gomez E et al, J Mol Cell Cardiol, 2012, 52: 1257-1264; Vercauteren M et al, Circulation, 2006, 114: 2498-2507). Briefly, a two-dimensional short axis view of the left ventricle was obtained at the level of the papillary muscle, in order to record M-mode tracings. LV diameters were measured by the American Society of Echocardiography leading-edge method from at least 3 consecutive cardiac cycles.

LV outflow velocity was measured by pulsed-wave and cardiac output (CO) was calculated as CO=aortic VTI×[π× (LV outflow diameter/2)$^2$]×heart rate, where VTI is velocity-time integral.

Measurements were performed by observers blinded to prior results and treatment groups.

Myocardial Perfusion

After 9 and 90 days of treatment, basal myocardial perfusion was assessed in methohexital-anesthetized animals using a Bruker Biospec 4.7 Tesla MRI, and using an acquisition T1 sequence that does not need contrast agent application, as previously described (Merabet N et al, J Mol Cell Cardiol, 2012, 52: 660-666; Banquet S et al, Circulation, 2011, 124: 1059-1170.) Briefly, the animals were positioned prone on an actively decoupled and warming pad with hot water circulation was used to maintain its physiological temperature. The ECG signal was monitored by placing two subcutaneous electrodes on each side of the rat at chest level. The electrodes were connected to an ECG trigger unit. As a feature of the trigger unit, both ECG and breath trigger pulses were derived from the observed signal containing both ECG and respiratory EMG signals. After standard adjustments, scout images were acquired to determine the short-axis plane for the perfusion imaging sequence. After optimization of the RF signal, the perfusion sequence was run allowing determination of myocardial tissue perfusion by Arterial Spin Labeling (ASL) technique, in which, the blood in the arteries upstream from the imaging volume is magnetically "labelled". As a consequence, image intensity changes occur depending on the blood supply to the tissue in the imaged slice. Upon subtraction of an image acquired without spin labelling, the background signal from static spins is removed and the difference image can be used to quantify perfusion. The difference of the inverse of the apparent T1 images then yields a measure of the regional Cardiac Blood Flow (rCBF) according to rCBF=L (1/T1sel-1/T1nonsel), where L is the blood-tissue partition coefficient.

Cardiac Hemodynamics

Left ventricle function was assessed using left pressure volume curves after 9 or 90 days of treatment, as previously described (Fang Y et al, J Mol Cell Cardiol., 2011, 51:168-176; Fang Y H et al, Journal of Cardiovascular Pharmacology, 2012, 59: 260-267). In brief, a 2F miniaturized combined conductance catheter-micromanometer (model SPR-819, Millar Instruments) connected to a pressure-conductance unit (MPCU-200, Millar) was advanced retrograde via the carotid artery into the left ventricle. This catheter has a micro-manometer surrounded by 4 platinum electrodes; the two outermost electrodes generate a current of 0.1 mA at a frequency of 20 kHz, which is sensed by the two innermost electrodes. Pressure-Volume (PV) loops were recorded at baseline and during loading by gently occluding the abdominal aorta with a cotton swab. Data were stored and analysed by using Millar conductance data acquisition and analysis software. Finally, the following parameters were measured/calculated from the pressure-volume curves:

Left ventricular end-diastolic pressure;
Left ventricular end-systolic pressure;
Left ventricular relaxation constant Tau;
Left ventricular end-diastolic pressure-volume relation; and
Left ventricular end-systolic pressure-volume relation.

Coronary Endothelial Function

Coronary endothelial function was assessed after 9 or 90 days of treatment, as described previously (Fang Y H et al, Journal of Cardiovascular Pharmacology, 2012, 59: 260-267; Mulder et al., Eur Heart J., 2008, 29:2171-2179). In brief, at the end of the left ventricular function assessment, the heart was removed and immediately placed in cold oxygenated Krebs buffer. A 1.5- to 2-mm-long segment of arteries were carefully dissected and mounted in a small vessel myograph. Normalization procedure was performed after an equilibration period. Segments with an internal diameter<170 μm was excluded to avoid mechanical endothelial injury and unspecific dysfunction. Concentration-response curves to acetylcholine ($10^{-8}$ to $3\times10^{-5}$ mol/L) were performed in serotonin-precontracted segments ($10^{-5}$ mol/L).

Cardiac Histology

At the end of the treatment period, the heart was taken out. After fixation, the left ventricle was cut in 3 sections of identical thickness. The sections of the heart were dehydrated and embedded in paraffin. 3 μm-thick sections were cut from each block and mounted on glass slides. Sections were stained with Sirius red for the determination of collagen. Slides were enlarged 500 times using a microscope connected to an image analysis system, as previously described (Mulder et al., J. Am. Coll. Cardiol., 1997). Collagen density was calculated in the left ventricle as the surface occupied by collagen divided by the surface of the image.

Plasma Nitrite Levels

Plasma nitrite measurements as a marker of NO production was performed using tri-iodide based chemiluminescence. The NO signal was quantified using a nitric oxide analyzer (NOA™ 280. Sievers Instruments Inc., Boulder, Colo., USA).

Left Ventricular Oxidative Stress

Left ventricular reactive oxygen species production level were evaluated in left ventricular homogenates (obtained after 9 or 90 days of treatment) by electron paramagnetic resonance spectroscopy (EPR) using the spin probe 1-hydroxy-3-methoxycarbonyl-2,2,5,5-tetramethylpyrrolidine (CMH, Noxygen, Germany), as previously described (Mulder P, Eur Heart J. 2008; 29:2171-2179). Stock solution of CMH (50 mM) were prepared in Krebs-HEPES buffer (0.1 M NaCl, 5 mM KCl, 2.5 mM CaCl2, 1.2 mM MgSO4, 25 mM NaHCO3, 1 mM KH2PO4, 5.6 mM D(+)-Glucose, 20 mM Na-HEPES, pH 7.4) containing 25 μM deferoxamine and 5 μM diethyldithiocarbamate. This stock solution of CMH was deoxygenated prior to the experiment in order to prevent CMH oxidation. After one hour of incubation in Krebs-HEPES buffer containing 2 mM ADP and the mitochondrial respiratory substrates, 10 mM glutamate and 4 mM malate, samples were frozen in a syringe in liquid nitrogen and kept at −80° C. until analysis. The oxidation of CMH into the stable 3-methoxycarbonyl-proxyl (CM•), driven mainly by superoxide and peroxynitrite reactions, was recorded using a MiniScope MS-200 X-band spectrometer (Magnettech, Germany). The EPR instrumental setting for field scan were as follows: Bo-field 3356.98 G, microwave power 1 mW, microwave attenuation 20 dB, modulation frequency 9.74 GHz, modulation amplitude 5 G, scan time 60 sec. Intensity of the spectra was measured from the height of the central line. CM• production was quantified using CP° standard and expressed in μmol of CM• per mg of total proteins.

Statistical Analysis

All results are given as mean±SEM.

In order to evaluate the effect of metabolic syndrome, all parameters obtained in untreated Zucker fa/fa and lean rats were compared by Student's unpaired two-tailed t-test. In order to evaluate the effects of long- or short-term imeglimin treatment, all parameters obtained in 9- and 90-day treated Zucker fa/fa rats were compared with time-matched untreated Zucker fa/fa using Student's unpaired two-tailed t-test.

Before applying parametric tests as Student's unpaired two-tailed t-test, the Gaussian distribution of data was assessed by Shapiro-Wilk normality test and Kolmogorov-Smirnov test and graphically by QQplot and normal probability plot.

Results

This preclinical study in a rat model of metabolic syndrome was designed to investigate imeglimin's protective effects on HFPEF. Indeed, obese Zucker fa/fa rats are known to develop cardiac dysfunctions which are very similar to the ones of HFPEF patients. The Zucker fa/fa rats were treated with 150 mg/kg imeglimin twice-daily for 9 or 90 days.

Figure 1A:
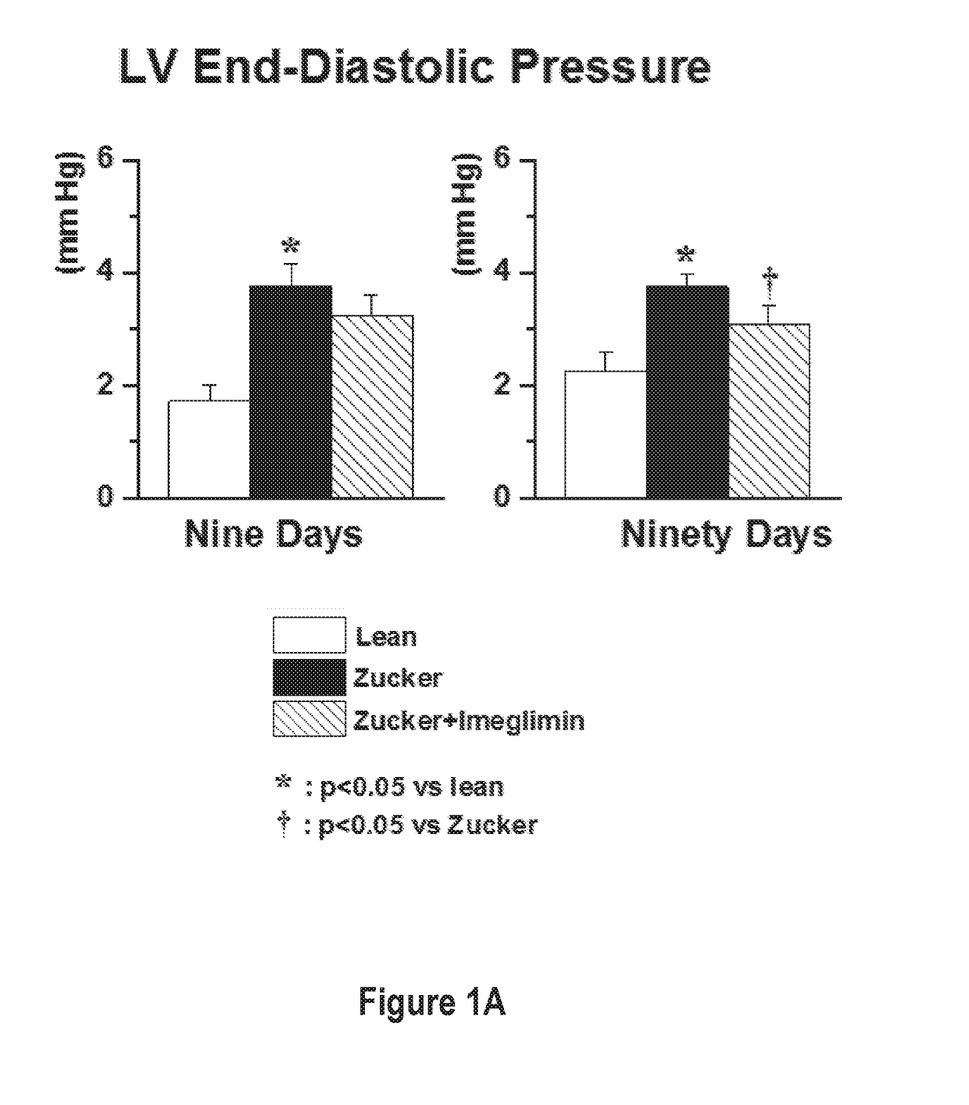
FIG. 1A: LV End-Diastolic Pressure after nine days (left) or ninety days (right) of treatment of lean rats with vehicle (white boxes), Zucker fa/fa rats with vehicle (black boxes), or Zucker fa/fa rats with imeglimin (crosshatched boxes).
Figure 1B:
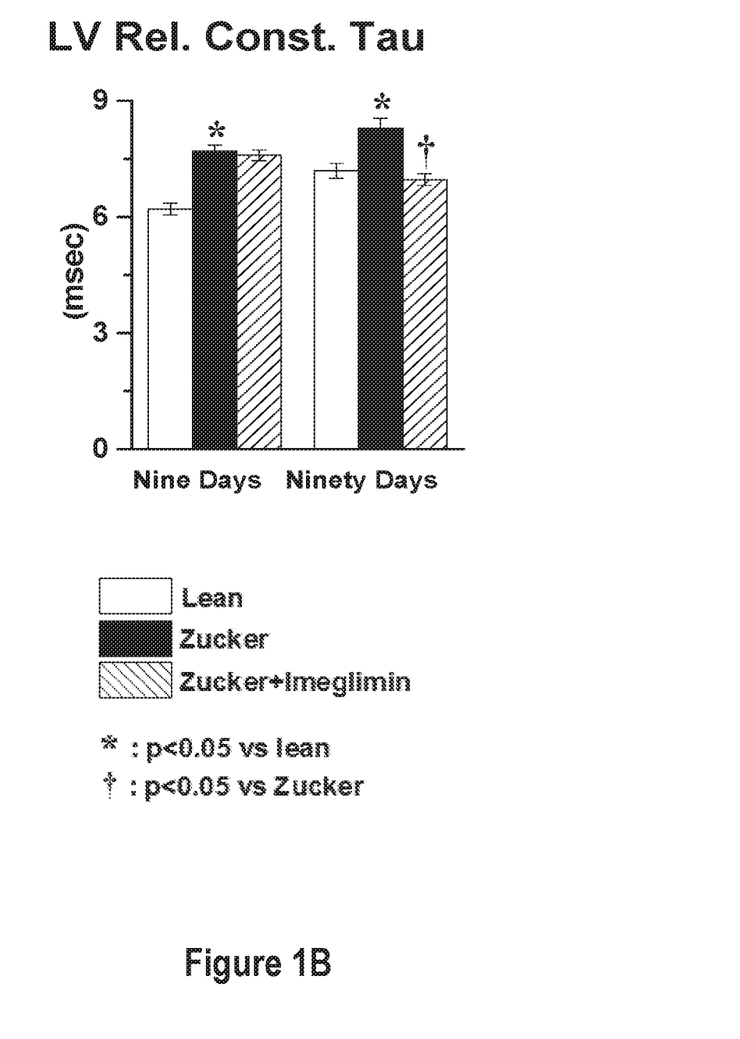
FIG. 1B: LV Relaxation Constant Tau after nine days (left) or ninety days (right) of treatment of lean rats with vehicle (white boxes), Zucker fa/fa rats with vehicle (black boxes), or Zucker fa/fa rats with imeglimin (crosshatched boxes).
Figure 1C:
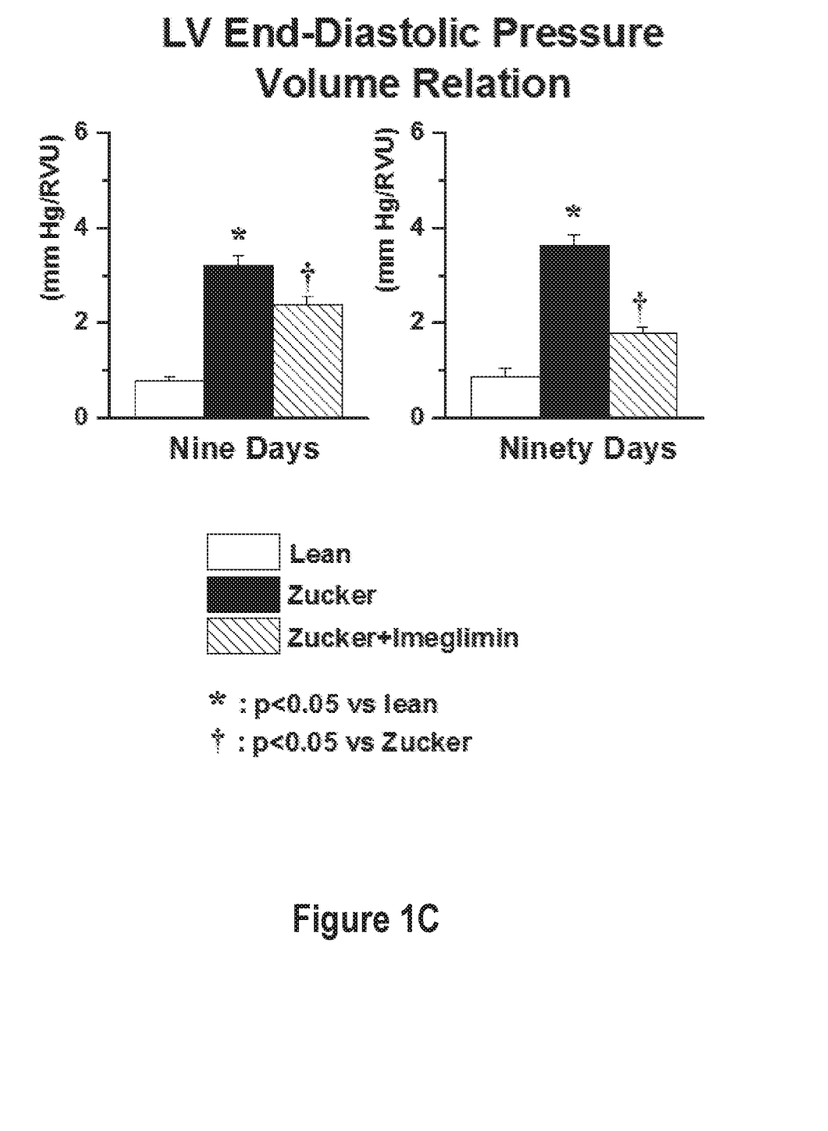
FIG. 1C: LV End-Diastolic Pressure Volume Relation after nine days (left) or ninety days (right) of treatment of lean rats with vehicle (white boxes), Zucker fa/fa rats with vehicle (black boxes), or Zucker fa/fa rats with imeglimin (crosshatched boxes).

13 and 24 weeks old untreated Zucker fa/fa rats present:
Left Ventricle diastolic dysfunction:
an increased LV end-diastolic pressure (cf. FIG. 1A);
an increased LV relaxation constant Tau (cf FIG. 1B); and
an increased LV end-diastolic pressure volume relation (cf. FIG. 1C).
associated with reduced cardiac output (cf FIG. 2A) and myocardial perfusion (cf. FIG. 2B).

These parameters are typical of HFPEF.

Figure 2A:
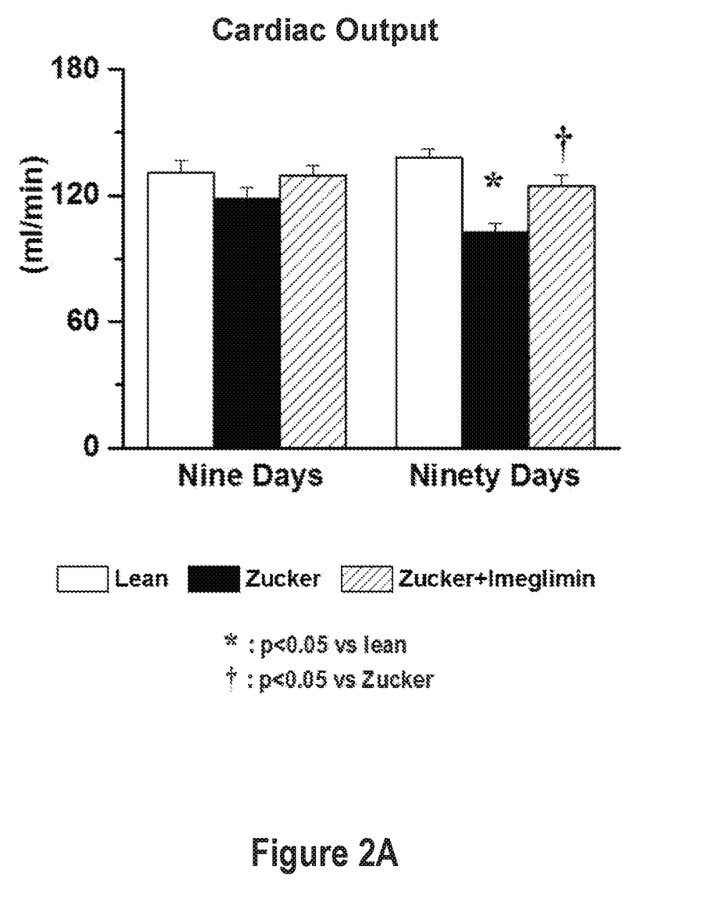
FIG. 2A: Cardiac Output after nine days (left) or ninety days (right) of treatment of lean rats with vehicle (white boxes), Zucker fa/fa rats with vehicle (black boxes), or Zucker fa/fa rats with imeglimin (crosshatched boxes).
Figure 2B:
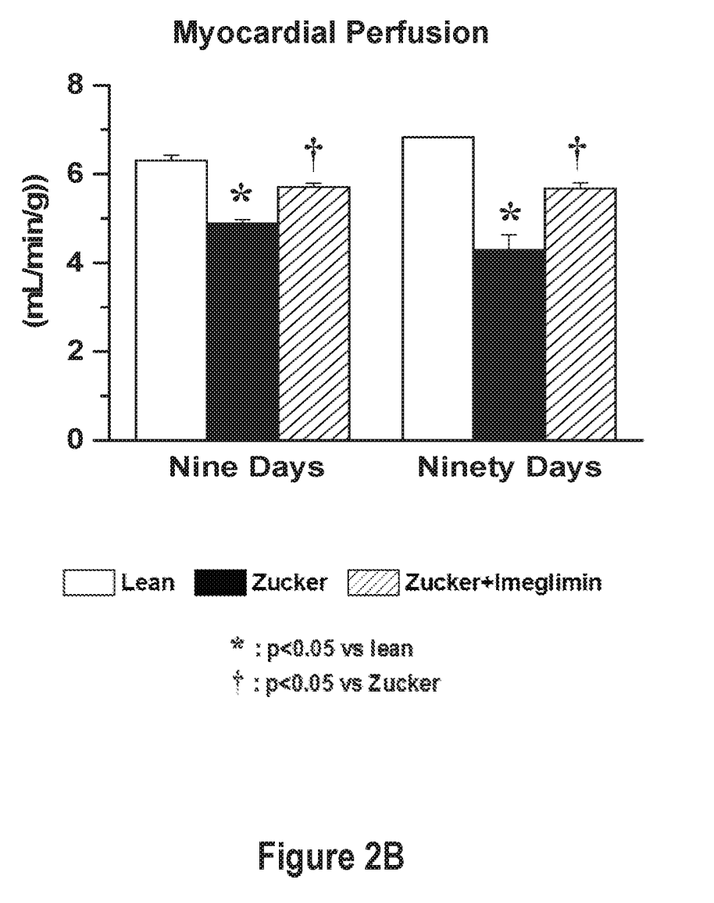
FIG. 2B: Myocardial Perfusion after nine days (left) or ninety days (right) of treatment of lean rats with vehicle (white boxes), Zucker fa/fa rats with vehicle (black boxes), or Zucker fa/fa rats with imeglimin (crosshatched boxes).

When Zucker fa/fa rats were treated with imeglimin during 90 days, a significant reduction of LV end-diastolic pressure (FIG. 1A), LV relaxation constant Tau (FIG. 1B) and LV end-diastolic pressure volume relation (FIG. 1C) were observed as well as an increased cardiac output and myocardial perfusion (cf. FIGS. 2A and 2B).

In particular, the increase in the myocardial perfusion and the reduction of the left ventricular end-diastolic pressure-volume relation were already significant after only 9 days of treatment.

The LV compliance was increased by about 50% after 90 days of treatment.

Figure 3:
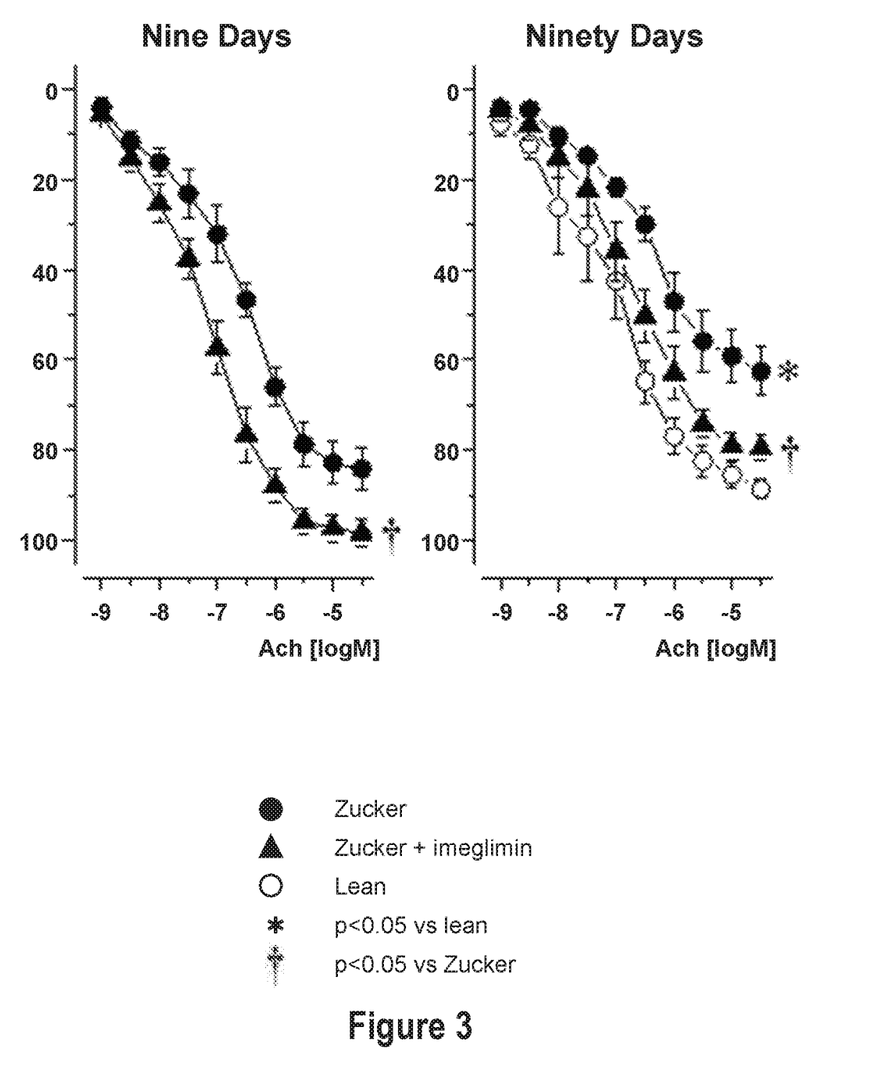
FIG. 3 shows septal coronary relaxation induced by acetylcholine after nine days (left) or ninety days (right) of treatment of Zucker fa/fa rats with vehicle (black circles) or Zucker fa/fa rats with imeglimin (black triangles). Twenty-four weeks-old untreated lean rats (white circle) were used as healthy control.

Moreover, imeglimin treatment was shown to improve coronary artery endothelium-dependent relaxation. Indeed, imeglimin administration for 9 and 90 days prevented the impairment in acetylcholine-induced relaxation of septal coronary artery observed in untreated Zucker fa/fa rats at 90 days (cf. FIG. 3).

In addition, the results show that LV interstitial collagen was significantly increased in 24-week old Zucker fa/fa rats when compared to lean rats (cf. Table 1). A 90-day administration of imeglimin significantly reduced LV collagen density (cf. Table 1). This reduced LV collagen accumulation probably contributes to the further improvement of LV compliance after long-term treatment with imeglimin.

LV reactive oxygen species (ROS) production was also increased, while plasma nitrite levels were decreased in 13- and 24-week-old untreated Zucker fa/fa rats when compared to lean rats (cf. Table 1). Both 9- and 90-day imeglimin treatment decreased ROS levels and increased plasma nitrite levels (cf. Table 1).

This observed reduction in LV tissue ROS production limits the neutralization of NO, resulting in an increased NO bio-availability as suggested by the increase of plasma nitrites. This increase of NO bio-availability likely contributes to the immediate improvement of LV diastolic dysfunction via direct and indirect mechanisms. Indeed, reduced myocardial NO bioavailability increases myocyte resting tension and impairs LV dysfunction (Van Heerebeek et al., Circulation., 2008, 117:43-51; Gillebert et al., Am J Physiol., 1992, 263:H857-865; Van Heerebeek et al., Curr Diab Rep., 2009, 9:79-86), while an increase in NO bio-availability/production induced via administration of its co-factor tetrahydrobiopterin, NO donors or endothelial NO synthase enhancers improves LV diastolic dysfunction (Silberman et al., Circulation., 2010, 121:519-528; Matter et al., Circulation., 1999, 99:2396-2401; Fraccarollo et al., Circulation., 2008, 118:818-827). Furthermore, an improved NO-bio-availability at the level of the coronary vasculature, as illustrated by the improvement of coronary endothelium dependent dilatation, might contribute to the improvement of LV diastolic dysfunction, via the increase in myocardial tissue perfusion observed after imeglimin treatment. Indeed, the normalization of myocardial perfusion by imeglimin probably prevents LV tissue hypoxia observed in Zucker fa/fa rats and subsequent activation of mechanisms inducing LV dysfunction.

TABLE 1

| | | | Zucker fa/fa | |
| --- | --- | --- | --- | --- |
| Group | Time | Lean | Untreated | Imeglimin |
| LV collagen density (%) | $D_9$ | — | — | — |
| | $D_{90}$ | 2.06 ± 0.11 | 3.07 ± 0.0.09* | 2.52 ± 0.20† |
| LV ROS production ($AU \cdot \mu g^{-1} \cdot h^{-1}$) | $D_9$ | 32.75 ± 0.97 | 39.51 ± 1.77* | 27.61 ± 1.29† |
| | $D_{90}$ | 26.69 ± 3.06 | 40.96 ± 3.29* | 34.02 ± 1.49† |
| Plasma nitrite (mM) | $D_9$ | 407 ± 20 | 270 ± 27* | 424 ± 15† |
| | $D_{90}$ | 450 ± 43 | 292 ± 27* | 438 ± 18† |

*$p < 0.05$ vs. Lean zucker fa/+;
†$p < 0.05$ vs. untreated Zucker fa/fa

This study demonstrates that very early in the course of treatment, imeglimin strongly improved the parameters of LV diastolic dysfunction in the Zucker fa/fa rats compared to untreated Zucker fa/fa rats, underlying a clear beneficial effect of imeglimin on the progression of HFPEF.

I claim:

1. A method for treating heart failure with preserved ejection fraction (HFPEF) in a patient suffering from HFPEF and having an ejection fraction superior or equal to about 45% and a diastolic dysfunction of at least grade I, wherein the method comprises daily administering to said patient by an oral route a therapeutically effective amount of imeglimin as an immediate release form, whereby diastolic dysfunction is improved.

2. The method according to claim 1, wherein the imeglimin is administered as a pharmaceutical composition comprising a therapeutically effective amount of imeglimin and at least one pharmaceutically acceptable carrier.

3. The method according to claim 1, wherein the patient is a human.

4. The method according to claim 3, wherein the human is a female human.

5. The method according to claim 3, wherein the patient is at least 50 years old.

6. The method according to claim 1, wherein the imeglimin is administered to the patient at an amount between about 10 mg/kg of body weight/day and about 100 mg/kg of body weight/day.

7. The method according to claim 1, wherein the amount of imeglimin is about 500 mg to about 3000 mg per day.

8. The method according to claim 7, wherein the amount of imeglimin is about 1000 mg to about 3000 mg per day.

9. The method according to claim 1, wherein imeglimin is administered orally.

10. The method according to claim 1, wherein imeglimin is administered once, twice, or three times per day.

11. The method according to claim 10, wherein imeglimin is administered once per day.

12. The method according to claim 1, wherein imeglimin is administered in the form of a free base or a pharmaceutically acceptable salt thereof.

13. The method according to claim 12, wherein imeglimin is administered in the form of a hydrochloride salt.

14. The method according to claim 1, wherein the patient suffering from HFPEF further has a comorbidity which is a metabolic syndrome selected from obesity, diabetes, type 2 diabetes, monogenic diabetes mellitus, and transient neonatal hyperglycemia.

15. The method according to claim 14, wherein the comorbidity is type 2 diabetes.

16. The method according to claim 1, wherein imeglimin is administered with a second pharmaceutical agent.

17. The method according to claim 16, wherein imeglimin is administered concomitantly with the second pharmaceutical agent.

18. The method according to claim 16, wherein imeglimin is administered sequentially with the second pharmaceutical agent.

19. The method according to claim 16, wherein the second pharmaceutical agent is an antidiabetic drug.

20. The method of claim 1 wherein the patient has a diastolic dysfunction of grade II, III or IV.

21. The method of claim 1, wherein the patient has a BNP blood concentration superior to about 35 pg/ml.

22. The method of claim 1 wherein the patient suffering from HFPEF is such that:
   a) the patient is at least 50 years old,
   b) the patient has an ejection fraction superior or equal to about 50%, and
   c) the patient has a BNP blood concentration superior to 50 pg/ml.

* * * * *